US008163010B1

(12) United States Patent  (10) Patent No.: US 8,163,010 B1
Hausen et al.  (45) Date of Patent: Apr. 24, 2012

(54) STAPLE-BASED HEART VALVE TREATMENT

(75) Inventors: Bernard A. Hausen, Redwood City, CA (US); Bryan D. Knodel, Flagstaff, AZ (US); Luke W. Clauson, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 145 days.

(21) Appl. No.: 12/132,170

(22) Filed: Jun. 3, 2008

(51) Int. Cl.
*A61F 2/24* (2006.01)
(52) U.S. Cl. ...................................... 623/2.32
(58) Field of Classification Search ................ 623/1.12, 623/1.36, 2.36, 2.37, 2.38, 2.4, 2.41; 606/75, 606/151
See application file for complete search history.

(56) References Cited

U.S. PATENT DOCUMENTS

| | | | |
|---|---|---|---|
| 4,586,503 A * | 5/1986 | Kirsch et al. ................. 606/155 |
| 4,932,965 A | 6/1990 | Phillips |
| 5,242,457 A * | 9/1993 | Akopov et al. ............... 606/144 |
| 5,607,442 A * | 3/1997 | Fischell et al. ............... 623/1.18 |
| 5,891,160 A | 4/1999 | Williamson, IV et al. |
| 6,001,127 A | 12/1999 | Schoon et al. |
| 6,254,615 B1 * | 7/2001 | Bolduc et al. ................. 606/142 |
| 6,409,758 B2 | 6/2002 | Stobie et al. |
| 6,413,274 B1 | 7/2002 | Pedros |
| 6,506,197 B1 | 1/2003 | Rollero et al. |
| 6,695,866 B1 | 2/2004 | Kuehn et al. |
| 6,726,716 B2 | 4/2004 | Marquez |
| 6,730,118 B2 | 5/2004 | Spenser et al. |
| 6,986,775 B2 | 1/2006 | Morales et al. |
| 7,285,131 B1 | 10/2007 | Bombard et al. |
| 7,344,544 B2 * | 3/2008 | Bender et al. ................. 606/139 |
| D574,956 S * | 8/2008 | Grim ........................... D24/145 |
| 7,473,258 B2 * | 1/2009 | Clauson et al. ............... 606/139 |
| 7,485,142 B2 * | 2/2009 | Milo ............................ 623/2.11 |
| 7,513,909 B2 * | 4/2009 | Lane et al. .................... 623/2.4 |
| 7,753,922 B2 * | 7/2010 | Starksen ....................... 606/144 |
| 7,918,873 B2 * | 4/2011 | Cummins ...................... 606/219 |
| 7,922,762 B2 * | 4/2011 | Starksen ....................... 623/2.11 |
| 2003/0195514 A1 | 10/2003 | Trieu et al. |
| 2004/0138705 A1 * | 7/2004 | Heino et al. .................. 606/219 |
| 2004/0167620 A1 | 8/2004 | Ortiz et al. |
| 2004/0236419 A1 * | 11/2004 | Milo ............................ 623/2.36 |
| 2004/0243230 A1 | 12/2004 | Navia et al. |
| 2004/0262461 A1 * | 12/2004 | Del Re et al. .................... 248/71 |
| 2004/0267310 A1 * | 12/2004 | Racenet et al. ................ 606/219 |
| 2005/0065601 A1 | 3/2005 | Lee et al. |
| 2005/0216079 A1 | 9/2005 | MaCoviak |
| 2005/0251252 A1 | 11/2005 | Stobie |
| 2005/0267572 A1 | 12/2005 | Schoon et al. |
| 2006/0015144 A1 * | 1/2006 | Burbank et al. ............... 606/219 |
| 2006/0025784 A1 * | 2/2006 | Starksen et al. ............... 606/151 |
| 2006/0106456 A9 | 5/2006 | Machold et al. |
| 2006/0253143 A1 * | 11/2006 | Edoga et al. .................. 606/153 |
| 2006/0282118 A1 * | 12/2006 | Surti ............................ 606/219 |

(Continued)

*Primary Examiner* — Todd Manahan
*Assistant Examiner* — Jonathan R Stroud
(74) *Attorney, Agent, or Firm* — Brian A. Schar

(57) ABSTRACT

A medical device for treating a heart valve may include a master staple and a loop fixed to the master staple prior to deployment of the master staple. The heart valve may be treated with that master staple and loop, and a plurality of follower staples that are independent from the loop prior to deployment of the master staple, by closing the master staple into the valve annulus, such that the point of the loop that is fixed to the master staple is fixed relative to the valve annulus, and engaging the loop with a plurality of follower staples after that closing.

5 Claims, 4 Drawing Sheets

U.S. PATENT DOCUMENTS

| | | |
|---|---|---|
| 2007/0010854 A1* | 1/2007 | Cummins .................... 606/219 |
| 2007/0129794 A1 | 6/2007 | Realyvasquez |
| 2007/0208360 A1* | 9/2007 | Demarais et al. ............. 606/153 |
| 2007/0219570 A1* | 9/2007 | Deem et al. ................... 606/151 |
| 2008/0051807 A1* | 2/2008 | St. Goar et al. .............. 606/139 |
| 2008/0058868 A1* | 3/2008 | To et al. ........................ 606/219 |
| 2008/0296344 A1* | 12/2008 | Cropper et al. ............ 227/176.1 |
| 2009/0039138 A1* | 2/2009 | Bender et al. .............. 227/179.1 |
| 2009/0318957 A1* | 12/2009 | Viola et al. .................... 606/219 |
| 2011/0178466 A1* | 7/2011 | Vioreanu et al. ............. 604/180 |

\* cited by examiner

STAPLE-BASED HEART VALVE TREATMENT

FIELD OF THE INVENTION

The invention relates to an apparatus and method for performing heart valve surgery.

BACKGROUND

Annuloplasty is a procedure that treats or reconstructs a cardiac valve, usually the mitral valve. An annuloplasty ring is a device that is commonly used in that procedure. Referring to FIG. 1 an annuloplasty ring is sutured into place, in or near the tissue of a valve annulus 4 of the heart 2, and acts to reduce the circumference of the valve annulus 4. The annuloplasty ring may be circular, shaped as a different closed shape, C-shaped, or shaped as another open shape, and may be rigid, semi-rigid or flexible. That ring is typically smaller in diameter than the valve 6 being treated, in order to reduce its circumference and make the valve 6 competent. While the treatment of valve disease or incompetence with an annuloplasty ring is safe and effective, the installation of that annuloplasty ring is time-consuming due to the need to suture the annuloplasty ring in place, and as a result the patient must spend an appreciable amount of time connected to a heart-lung machine with the heart arrested during the operation.

BRIEF DESCRIPTION OF THE DRAWINGS

The use of the same reference symbols in different figures indicates similar or identical items.

DETAILED DESCRIPTION

Figure 2:
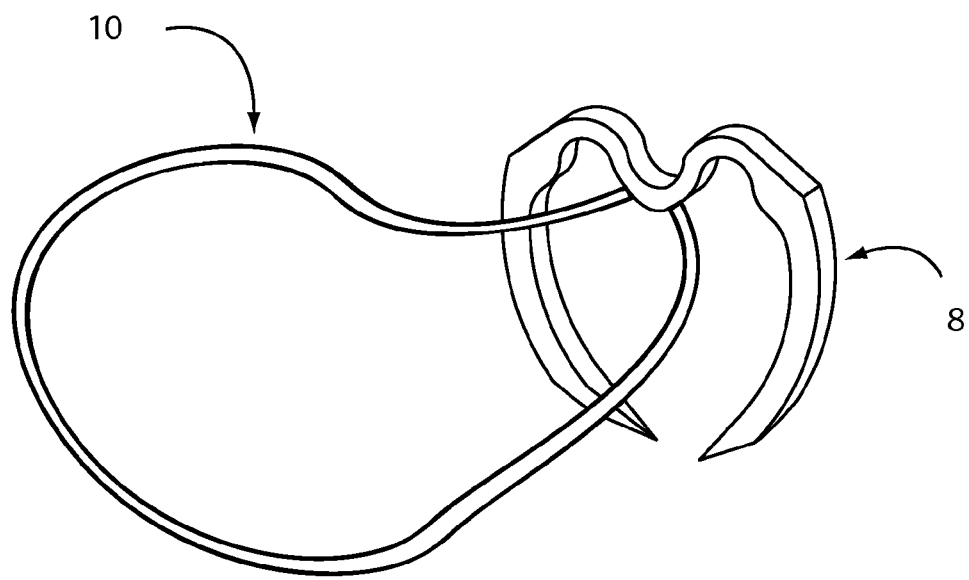
FIG. 2 is a perspective view of an exemplary master staple with a loop fixed thereto.

Referring to FIG. 2, a loop 10 is attached to the master staple 8. The loop 10 may be attached to any suitable location or portion of the master staple 8, such as the base of the master staple 8. The loop 10 may be fabricated from metal, plastic or other biocompatible material. As one example, the loop 10 may be metallic wire. As another example, the loop 10 may be suture. The entirely of the loop 10 may be flexible, or the loop 10 may include multiple rigid segments connected by flexible segments. Alternately, at least part of the loop 10 may be fabricated from rigid elements connected to one another in the manner of a chain, such that the loop 10 as a whole is generally flexible. Advantageously, the loop 10 is fixed to the master staple 8, in any suitable manner. As one example, the loop 10 and the master staple 8 are fabricated as an integral unit. As another example, the loop 10 is fabricated from a length of material having two ends, and both ends are fastened to the master staple 8 such as by welding, adhesive, or any other suitable manner. Where the loop 10 is fabricated from a length of suture, the ends of the suture may be tied to the master staple 8 to form the loop 10. Advantageously, the loop 10 is not only fixed to the master staple 8, but also nondetachable from the master staple 8.

Figure 3:
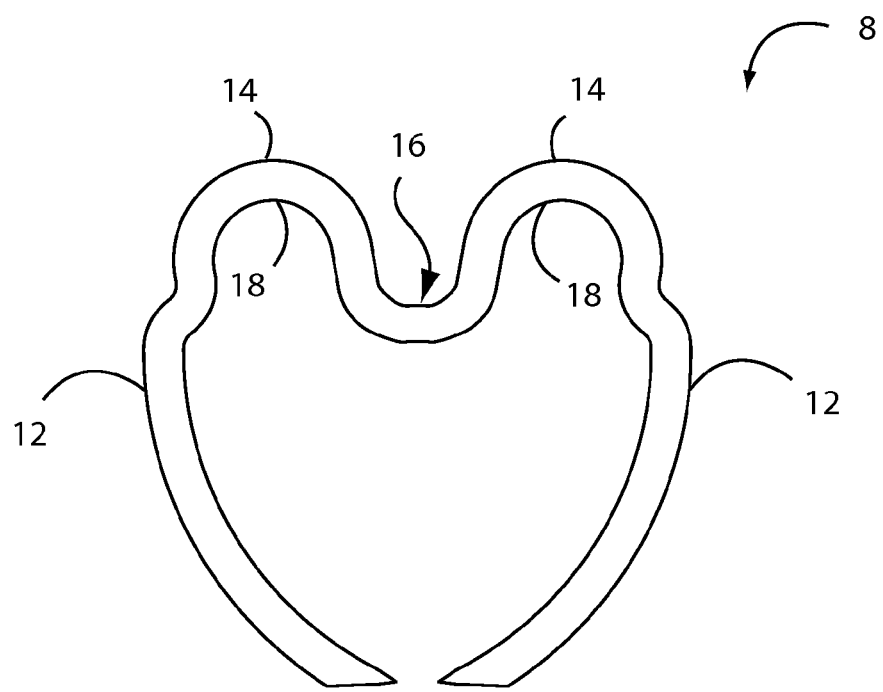
FIG. 3 is a top view of the master staple of FIG. 2, without the loop.

The master staple 8 may be sized and shaped in any suitable manner. As one example, referring also to FIG. 3, the master staple 8 may be substantially as disclosed in U.S. Pat. No. 7,344,544, which is hereby incorporated by reference in its entirety. The master staple 8 may have a curved M-shape. However, the master staple 8 may have any other suitable shape. The master staple 8 may have two tines 12, each extending at least partially in the distal direction. The tines 12 may be curved, and may each have a shape and radius of curvature such that the tines 12 are generally not parallel to one another. The radius of curvature may be substantially coincident with the path of travel of the tines 12 during closure of the master staple 8. The master staple 8 may be substantially bilaterally symmetrical, although it may be asymmetrical if desired. The master staple 8 may be a substantially continuous solid. As used in this document, the term "solid" means that a structure has no slots, holes, apertures or other enclosed or bounded openings defined therein.

The distal end of each tine 12 may have a substantially pointed or sharpened distal end. However, the distal ends of the tines 12 need not be pointed or sharpened, particularly if the cross-sectional area of each tine 12 is small. Advantageously, each tine 12 has a single distal end that is not bifurcated or otherwise forked or split. The body of the master staple 8 extends proximally from the distal end of one tine 12 and curves or angles toward the longitudinal centerline of the master staple 8. This curve may extend outward from the longitudinal centerline of the master staple 8, then toward the longitudinal centerline of the master staple 8. Alternately, the tine 12 may curve differently. The body of the master staple 8 reaches a peak 14, then extends distally and toward the longitudinal centerline of the master staple 8. The body of the master staple 8 then reaches a trough 16, then extends proximally and away from the longitudinal centerline of the staple to a second peak 14. The body of the master staple 8 continues distally to form the second tine 12, and ends at the distal end of the second tine 12. Alternately, the master staple 8 may be shaped differently. For example, the master staple 8 may have more than two tines 12. A valley 18 is the area on the master staple 8 on the other side of the master staple 8 from a peak 14. For example, where a peak 14 of the master staple 8 includes a convex curve oriented proximally, the corresponding valley 18 is a concave curve opening distally. Advantageously, the master staple 8 is substantially solid.

The master staple 8 may lie substantially in a single plane. That is, the master staple 8 is shaped such that a single plane extends through and substantially bisects the entire master staple 8. Alternately, the master staple 8 does not lie substantially in a single plane. The longitudinal and lateral dimensions of the master staple 8 overall may both be substantially larger than the height of the master staple 8. Alternately, the master staple 8 may be sized differently. The master staple 8 may be plastically deformable. If so, the master staple 8 may be fabricated from stainless steel, titanium or any other suitable plastically-deformable material. Alternately, the master staple 8 may be elastically deformable. If so, the master staple 8 may be fabricated from nickel-titanium alloy or any other suitable elastic or superelastic material. The master staple 8 may be fabricated from a single wire or other piece of material, having a rectangular, circular or other cross-section. The cross-section of the master staple 8 may be substantially constant along the entire master staple 8, or may vary at different locations along the master staple 8. For example, the cross-sectional area of the master staple 8 at certain locations may be less than at other locations, in order to promote bending in those locations having a lesser cross-sectional area.

The loop 10 may extend from any suitable part or parts of the master staple 8. As one example, referring back to FIG. 2, the loop 10 may extend from the trough 16 of the master staple 8, and/or a location in proximity to the trough of the master staple 8. As another example, the loop 10 may extend between peaks 14 of the master staple 8, such that one end of the loop 10 is connected to one peak 14 and the other end of the loop 10 is connected to the other peak 14. As another example, the loop 10 may extend between the tines 12 of the master staple 8, such that one end of the loop 10 is connected to one tine 12 and the other end of the lop 10 is connected to the other tine 12. As another example, one end of the loop 10 may be connected to one of the tines 12, to one of the peaks 14, or to the trough 16, and the other end of the loop 10 may be connected to one of the tines 12, to one of the peaks 14, or to the trough 16. The loop 10 may have any suitable length. If the loop 10 is fixed to the master staple 8 prior to surgery, the master staple 8 may be available with different predefined lengths of the loop 10, each appropriate for a different circumference of valve annulus, such that a range of anatomically-differing patients may be treated. As another example, one end of the loop 10 may be attached to the master staple 8 by the surgeon at the time of the surgery, such as by tying, thereby allowing the surgeon to customize the length of the loop 10 according to the needs of the individual patient. After the loop 10 has been captured by one or more follower staples 20, the other end of the loop 10 may be tied to the master staple. As another example, the loop is not attached to the master staple 8 until the loop 10 has been fixated to the valve annulus 4 with the follower staples 20 described below. Any excess length of the loop 10 may then be cut and removed after final fixation to the master staple 8.

Figure 4:
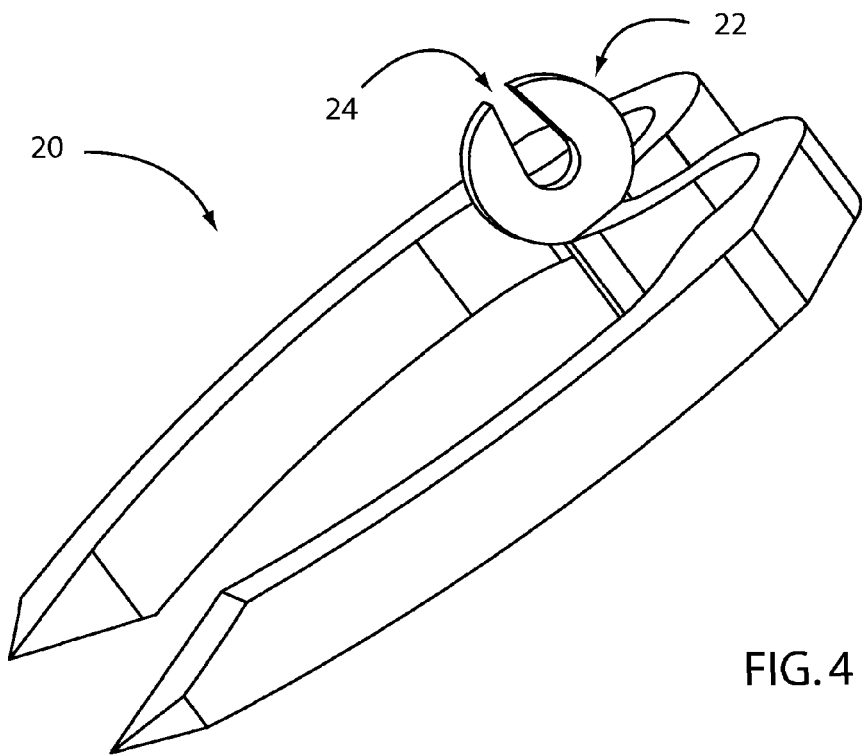
FIG. 4 is a perspective view of an exemplary follower staple.
Figure 5:
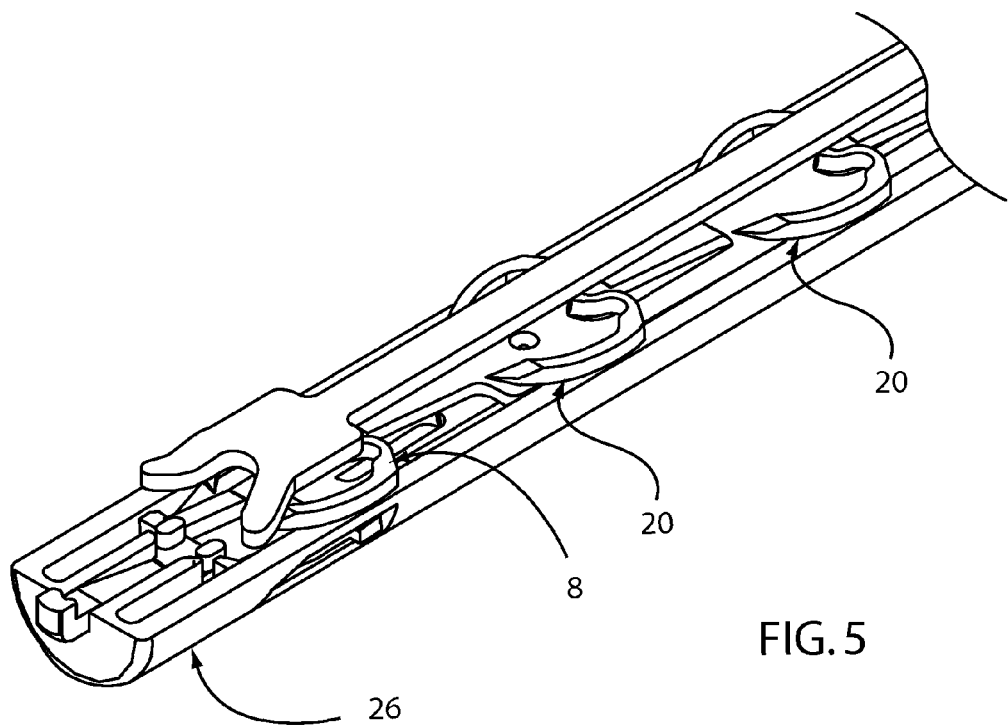
FIG. 5 is a perspective view of an exemplary effector that holds and deploys the master staple and follower staples.

Referring to FIG. 4, a follower staple 20 is configured substantially in the same way as the master staple 8 described above, with the addition of an engagement feature 22. The engagement feature 22 may be configured in any manner to engage the loop 10 of the master staple 8 before and/or during deployment of the follower staple 20, as described in greater detail below. As one example, the engagement feature 22 may be generally U-shaped, with a notch 24 defined between the arms of the U-shape that has a width substantially equal to the thickness of the loop 10. As another example, the open end of the notch 24 may have a width slightly less than the thickness of the loop 10, such that the loop 10 is compressed to press it into the notch 24, and such that the engagement feature 22 retains the loop 10 after it has been inserted into the notch. The follower staple 20 is independent from the loop 10 prior to deployment. Optionally, the engagement feature 22 may be omitted from the follower staple 20, and the follower staple 20 may engage the loop 10 of the master staple 8 by closing around that loop 10. The follower staples 20 may be substantially the same size as the master staple 8. Alternately, the follower staples 20 may be sized and/or shaped in a different manner than the master staple 8. The engagement feature 22 on the follower staple 20 may provide a firm attachment to the loop 10, regardless of the variable amount of tension or stress placed on the loop 10 during a normal deployment. Alternately, the engagement feature 22 of at least one follower staple 20 may engage the loop 10 less firmly, such that the loop 10 may be adjustable relative to at least one follower staple 20 after placement of some or all of the loop 10, to allow for optimal length distribution of the loop 10 over the entire circumference of the valve annulus 4.

An effector 26 holds the master staple 8 and a plurality of follower staples 20 prior to deployment. The master staple 8 is located distal to the follower staples 20, such that the master staple 8 is deployed first, as described in greater detail below. The effector 26 may be configured in any suitable manner. As one example, the effector 26 may be configured substantially as described in U.S. patent application Ser. No. 11/672,858, filed on Mar. 8, 2007, which is hereby incorporated by reference in its entirety. The loop 10 of the master staple 8 may be held completely within the effector 26 prior to deployment.

Operation

Figure 1:
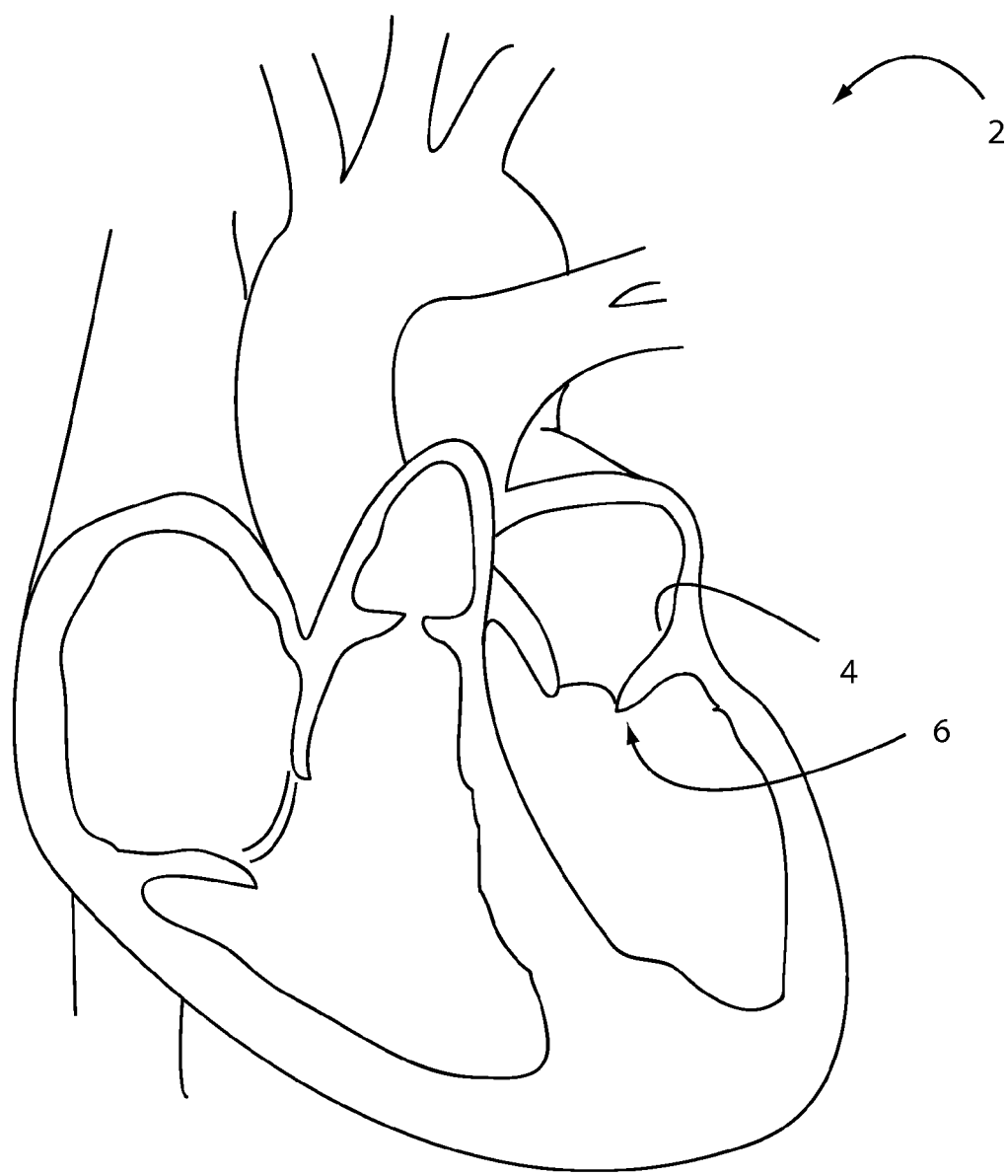
FIG. 1 is a cross-section view of a human heart.

Referring to FIG. 1, the physician gains access to the heart valve 6 to be reinforced or replaced in any suitable manner. Advantageously, the physician approaches the heart valve 6 through the vasculature, in an interventional procedure. In an interventional procedure, the heart 2 may continue to beat during the procedure; alternately, the heart 2 may be stopped and the patient placed on a heart-lung machine. Such a procedure may be performed by an interventional cardiologist or other professional. Alternately, the physician may approach the heart valve 6 through the wall of the heart 2, in an open surgical procedure. If so, the heart 2 is stopped and the patient placed on a heart-lung machine during the procedure. Such a procedure may be performed by a cardiac surgeon or other professional. Both interventional and surgical approaches to a heart valve 6 are standard in the art. For clarity, the interventional approach is described herein. The heart valve 6 may be any of the valves of the heart 2, such as but not limited to the mitral valve. The effector 26 is moved into the heart 2 and then into proximity to the valve annulus 4 of the heart valve 6 to be treated, such as along a catheter or a guidewire. The portion of the effector 26 out of which staples 8, 10 are deployed is placed adjacent to or in proximity to the valve annulus 4. The effector 26 may be controlled in any suitable manner in order to place staples 8, 20 into selected locations of the valve annulus 4. For example, part of the effector 26 may be rotatable relative to a remainder of the effector 26, and/or may be configured to be placed at two or more angles relative to a remainder of the effector 26, upon direct or remote control by an operator.

With the effector 26 positioned in proximity to the valve annulus 4, the master staple 8 is ready for deployment. Advantageously, the master staple 8 is splayed, then closed. The master staple 8 may be moved longitudinally after it has been splayed and before it is closed. However, the master staple 8 need not be splayed prior to closure. Examples of such splaying, closing and longitudinal motion are provided in U.S. Pat. No. 7,344,544 and in U.S. patent application Ser. No. 11/672,858, filed on Mar. 8, 2007, both of which are hereby incorporated by reference in their entirely. Motion of the distal ends of the tines 12 of the master staple 8 apart from one another, each in a direction away from the longitudinal centerline of the master staple 8, is referred to as "splaying." Splaying may be performed by holding the valleys 18 in a substantially fixed position, and applying a distal force to the trough 16 of the master staple 8 at a location closer to the longitudinal centerline of the master staple 8 than the location at which the valleys 18 are held. Alternately, splaying may be performed in any other suitable manner.

Next, the master staple 8 is advanced relative to the valve annulus 4 such that the tines 12 penetrate into the tissue of the valve annulus 4. The effector 26 may be held substantially stationary relative to the valve annulus 4, and the master staple 8 may be advanced along the effector 26 into tissue. As another example, the effector 26 as a whole may be moved closer to the valve annulus 4 after splaying the master staple 8, until the tines 12 penetrate the tissue of the valve annulus 4;

if so, the master staple 8 need not be movable relative to the effector 26 between splaying and closing.

Figure 6:
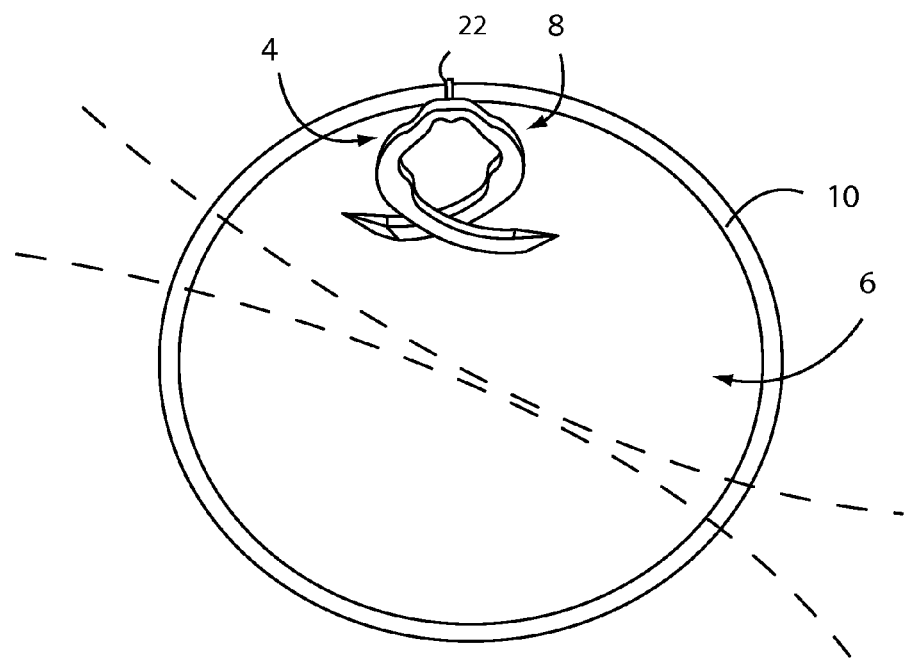
FIG. 6 is a perspective view of the master staple of FIG. 2 deployed into tissue of the valve annulus.

Next, the effector 26 is actuated to close the master staple 8, attaching the master staple 8 to the valve annulus 4, as shown in FIG. 6, in which the valve 6 is shown in phantom. During closing, the distal end of the tines 12 of the master staple 8 move toward one another, and may then swipe past one another and move away from one another. Closing may be performed by holding the trough 16 of the master staple 8 in a substantially fixed position, and applying a distal force to the peaks 14 of the staple 8 at a location further from the longitudinal centerline of the master staple 8 than the location at which the trough 16 is held. Alternately, closing may be performed in any other suitable manner. Because the master staple 8 is fixed in position relative to the valve 6, the point on the loop 10 that is fixed to the master staple 8 is fixed in position relative to the valve 6 as well. The remainder of the loop 10 is free relative to the valve 6.

Next, the follower staples 20 held by the effector 26 are sequentially deployed. Because the follower staples 20 are individually deployed, the surgeon has the option to place the follower staples 20 in any order or location on the valve annulus 4, to ensure successful placement and distribution of the loop 10 and thereby ensure successful treatment. The follower staples 20 may be shaped substantially the same as the master staple 8, and may be splayed and closed in substantially the same way. Alternately, the follower staples 20 are splayed and closed in a different way. The follower staples 20 may advance distally relative to the effector 26 after splaying and before closing, or may be substantially stationary relative to the effector 26 after splaying and before closing. Alternately, at least one of the follower staples 20 need not be splayed before closing. The engagement feature 22 of each follower staple 20 is moved into engagement with the loop 10 of the master staple 8 before closure of that follower staple 20. The engagement feature 22 of a follower staple 20 may engage the loop 10 before or after splaying of that follower staple 20. The engagement feature 22 may engage the loop 10 in any suitable manner. As one example, where the engagement feature 22 includes a notch 24, the engagement feature 22 is moved toward the loop 10 until the notch 24 receives the loop 10. The loop 10 may have a thickness slightly greater than the width of the notch 24, such that the loop 10 is compressed by its entry into the notch 24, and thereby is held securely by the notch 24 after its capture. However, the engagement feature 22 may engage the notch 24 in any suitable manner. Engagement between the engagement feature 22 of the follower staple 20 and the loop 10 may be visualized by fluoroscopy or by any other suitable method. Alternately, at least one follower staple 20 engages the loop 10 during its closure, where the loop 10 is trapped between the follower staple 20 and the tissue of the valve annulus 4, and the tines 12 of the follower staple 20 close around the loop 10. If so, the engagement feature 22 may be omitted from the follower staple 20.

Figure 7:
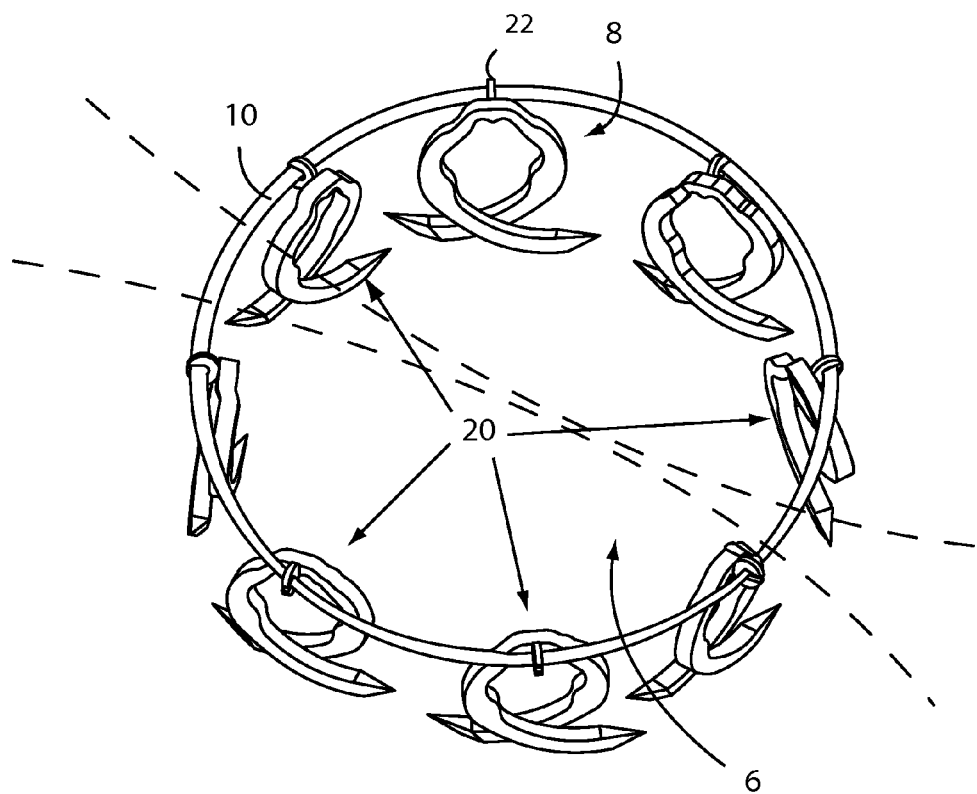
FIG. 7 is a perspective view of the master staple of FIG. 2 and follower staples of FIG. 4 deployed into tissue of the valve annulus.

Referring also to FIG. 7, the follower staples 20 are placed around a circumference of the loop 10, holding the loop 10 in a generally circular or elliptical shape. As shown, eight follower staples 20 are used, but more or fewer may be used depending on the size of the follower staples 20, the diameter of the valve annulus 4, the length of the loop 10, the discretion of the physician, and/or other factors. After all of the follower staples 20 have been placed, the loop 10 reinforces the valve annulus 4. The loop 10 has a fixed length, and the follower staples 20 are used to hold that loop in a fixed position with a fixed circumference, and as a result the loop 10 reduces the effective circumference of the valve to the circumference of the loop 10. In this way, the effectiveness of the valve 6 is improved. The effector 26 is then withdrawn from the heart 2, and the procedure is complete.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Further, the invention is not limited to the performance of heart valve surgery. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A method performed on a heart having a valve with a valve annulus, comprising:
    providing a master staple, a loop, and a plurality of follower staples;
    connecting said loop to said master staple;
    closing said master staple into the valve annulus only after said connecting, such that the point of said loop fixed to said master staple is fixed relative to the valve annulus; and
    engaging the valve annulus and said loop with said plurality of follower staples only after said connecting and said closing said master staple;
    wherein said follower staples are separate and independent from said loop prior to said closing of said master staple; and
    wherein said connecting comprises tying one end of said loop to said master staple before said engaging and tying the other end of said loop to said master staple after said engaging.

2. The method of claim 1, further comprising splaying said master staple before said closing.

3. The method of claim 2, further comprising providing an effector configured to hold and deploy said master staple and said follower staples; and further comprising advancing said master staple relative to said effector after said splaying and before said closing.

4. The method of claim 1, further comprising providing an effector configured to hold and deploy said master staple and said follower staples; and further comprising introducing said effector into the heart interventionally.

5. The method of claim 1, wherein said follower staples each include a notched engagement feature, and wherein said engaging includes receiving said loop into each said notch.

\* \* \* \* \*